United States Patent [19]

Cartmell

[11] Patent Number: 5,191,887
[45] Date of Patent: Mar. 9, 1993

[54] ASSEMBLY FOR DISPENSING TAB ELECTRODES

[75] Inventor: James V. Cartmell, Xenia, Ohio

[73] Assignee: NDM Acquisition Corp., Minneapolis, Minn.

[21] Appl. No.: 915,314

[22] Filed: Jul. 20, 1992

Related U.S. Application Data

[62] Division of Ser. No. 708,741, May 31, 1991.

[51] Int. Cl.⁵ .................................. A61B 5/0402
[52] U.S. Cl. ....................................... 128/640
[58] Field of Search ........................ 128/639–641, 128/798, 802, 803; 606/32

[56] References Cited

U.S. PATENT DOCUMENTS

| | | | |
|---|---|---|---|
| 4,653,502 | 3/1987 | Inoue et al. | 128/640 |
| 4,674,511 | 6/1987 | Cartmell | 128/640 |
| 4,727,881 | 3/1988 | Craighead et al. | |
| 4,757,817 | 7/1988 | Healy | 128/641 |
| 4,777,954 | 10/1988 | Keusch et al. | 128/641 X |
| 4,798,208 | 1/1989 | Faasse, Jr. | |
| 4,798,642 | 1/1989 | Craighead et al. | |
| 5,133,356 | 7/1992 | Bryan et al. | 128/640 |

*Primary Examiner*—Lee S. Cohen
*Attorney, Agent, or Firm*—Killworth, Gottman, Hagan & Schaeff

[57] ABSTRACT

An assembly for dispensing electrodes used in conjunction with electrocardiograph apparatus is provided. The assembly comprises a carrier sheet having two generally parallel and longitudinal tear lines extending along the carrier sheet, and a plurality of electrodes each having a projecting tab. The electrodes are mounted on the carrier sheet over the tear lines in two rows which are substantially parallel. The electrodes are oriented with their respective tabs extending away from the center of the carrier sheet, wherein the electrodes are exposed successively as the carrier sheet is torn along the tear lines thereby facilitating access to the tabs of the electrodes. The invention also provides an assembly comprising a carrier sheet, a pull strip releasably mounted along the longitudinal center of the carrier sheet, and a plurality of electrodes each having a projecting tab. The electrodes are mounted on the carrier sheet over the tear lines and oriented with their respective tabs extending away from the center of the carrier sheet, wherein the electrodes are exposed successively as the pull strip is pulled upwardly from the carrier sheet to facilitate access to the tabs of the electrodes.

9 Claims, 2 Drawing Sheets

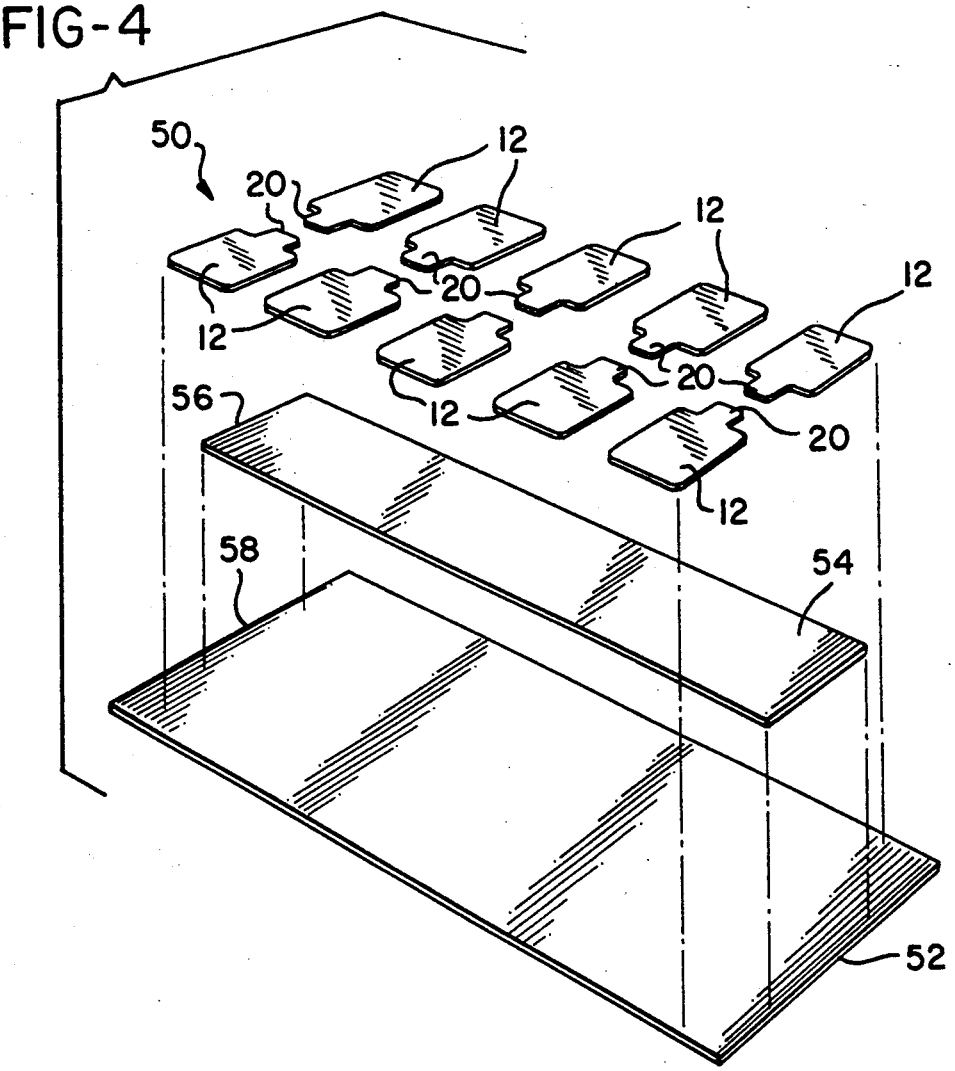
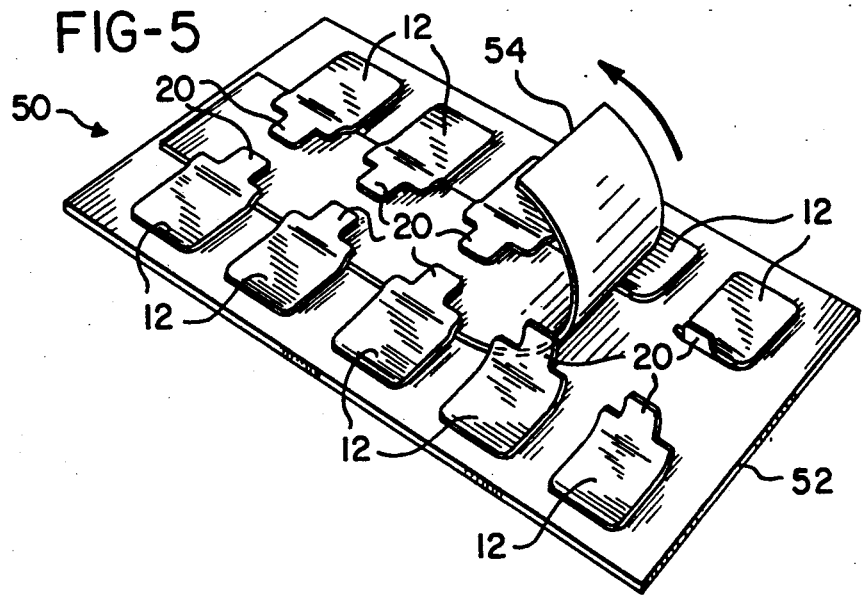

ASSEMBLY FOR DISPENSING TAB ELECTRODES

This is a divisional of application Ser. No. 07/708,741 filed May 31, 1991.

BACKGROUND OF THE INVENTION

The present invention relates to medical electrodes used in conjunction with electrocardiograph apparatus and more particularly, to an assembly for dispensing the medical electrodes.

Medical electrodes of the foregoing type are utilized in a number of applications for a variety of purposes. The monitoring of physiological electric potentials to detect muscular activity of the heart muscle is generally well established, such apparatus being referred to in the art as electrocardiograph (also referred to herein as ECG) apparatus. The resulting traces derived from such apparatus provide a diagnostic tool for detecting heart disease and/or defects. The monitoring of physiological electrical potentials may be employed in a number of other applications. For example, a simple ECG test to obtain a single tracing for diagnostic purposes may be carried out in a few minutes in a physician's office. Hence, medical electrodes utilized for such testing may be of a relatively simple disposable variety, since they are only in service for a very short time. Conversely, longer term monitoring applications require that the medical electrodes remain in place on the patient's skin for considerably extended periods of time. For example, in stress testing, the heart activity of the patient is monitored over a relatively longer period of time while the patient exercises upon a tread mill or similar apparatus. Such testing may include monitoring of the heart activity during the exercise, as well as continued monitoring during the rest period thereafter so as to monitor the return of the heart to a normal or unstressed condition. Similarly, medical electrodes monitoring heart activity during surgery may be required to remain in place and operational for a period of several hours.

During one of these electrocardiographic examinations, medical electrodes are connected to electrocardiograph apparatus are affixed to the skin of a patient at the proper positions for heart monitoring. It is important to not only properly position the electrodes on the patient, but also, to do so without excessive handling. Any additional handling of the electrode increases the tendency of having the electrode contaminated or otherwise disturbed, thereby destroying or altering the electrocardiograph trace resulting from the examination.

A common medical electrode used for these purposes typically comprise a relatively thin backing layer, a metal layer and a tacky conductive gel. For example, an electrode having a polyethylene terephthalate backing member with a tin foil layer and a conductive gel may be used for monitoring a patient for short periods of time. These medical electrodes commonly include a projecting tab and are thus referred to in the art as tab electrodes. The tab electrodes are mounted in rows on a carrier sheet for storage and dispensing with their conductive gel layers pressed against the sheet. Such electrodes do not adhere well to the patient and are difficult to use. As a result, some tab electrodes leave the tab portion of the electrode uncoated with conductive gel so as to allow the user to grip the electrode before removal from the carrier sheet.

Some users attempt to attach the lead wire clip from the electrocardiograph to the tab of the electrode before removing the electrode from the carrier sheet. This method requires a significant amount of care and is not accomplished easily or quickly. In particular, the user must carefully separate the uncoated tab of the electrode from the carrier sheet in order to permit attachment of the lead wire clip. The user must then peel the electrode from the sheet, transfer it to the patient in the proper position without dislodging the lead wire clip. In view of the rather small, thin and slippery construction of the backing and metal layers, users are faced with a formidable task.

Consequently, some users attach the electrode to the patient and thereafter, attach the lead wire to the tab of the electrode. In this way, the electrode can be removed from the carrier sheet more easily. Many difficulties, however, present themselves to users employing this procedure. For example, the separation of the electrode from the carrier sheet is difficult in view of the adhesive forces between the electrolyte gel of the electrode and the carrier sheet. As a response to these problems, U.S. Pat. No. 4,798,208 provides an assembly for dispensing electrodes which includes a release web and a fold line allowing the web to be folded back along its longitudinal center, thereby exposing the tabs of the electrodes. The electrodes, however, must be disposed on the web in two rows with the tabs of each electrode in each row facing one another. Moreover, if the electrodes include tabs having a tacky material such as an electrolyte gel on their undersurfaces, the tabs are not easily exposed by merely folding back the web along its longitudinal center. Therefore, it would be desirable to have a more versatile assembly for dispensing electrodes including those electrodes having tabs with tacky undersurfaces.

Accordingly, there is a need for an assembly for dispensing medical electrodes used in conjunction with electrocardiograph apparatus which facilitates access to the medical electrodes such that they may be easily removed and placed on a patient. There is also a need for a versatile assembly for dispensing medical electrodes which facilitates access to the electrodes without substantially increasing the cost of such an assembly.

SUMMARY OF THE INVENTION

The present invention meets the aforementioned needs by providing an assembly for dispensing medical electrodes used in conjunction with electrocardiograph apparatus. The assembly facilitates access to the medical electrodes by providing a means for exposing the tab surfaces of the medical electrodes while they are affixed to the carrier sheet of the assembly. This allows for easy access to the electrodes such that users may attach the electrodes to the skin of a patient quickly and precisely. Moreover, the aforementioned needs are met in that the assembly of the invention is not substantially more expensive than the assemblies used in the past.

Accordingly, in one aspect of the invention, the needs are met by an assembly for dispensing medical electrodes which comprises a carrier sheet having a longitudinal tear line spaced from the center of the carrier sheet and an electrode having a projecting tab. The electrode is mounted on the carrier sheet such that the electrode overlies the tear line, whereby the carrier sheet may be torn along the tear line to facilitate access to the electrode. The tear line is defined herein to comprise perforated lines, lines of weakening, cut lines, scored lines and other similarly classified lines of demarcation. The assembly may include a plurality of electrodes arranged on the carrier sheet in two (also referred to herein individually as first and second rows) which are substantially parallel. The plurality of electrodes each include the projecting tab and are oriented with their respective tabs extending away from the center of the carrier sheet. The electrodes in the two rows are exposed successively as the carrier sheet is torn along the tear lines, thereby facilitating access to the tabs of the electrodes.

In accordance with another aspect of the invention, the needs are met by yet another assembly for dispensing electrodes which is used in conjunction with electrocardiograph apparatus. The assembly comprises a carrier sheet, a pull strip releasably mounted along the longitudinal center of the carrier sheet, and an electrode having a projecting tab. The electrode is mounted on the carrier sheet such that the tab at least partially overlies the pull strip, whereby the pull strip may be pulled upwardly to expose the electrode for access thereto. The assembly may include a plurality of electrodes each having the projecting tab and being mounted on the carrier sheet in two rows such that the tabs of the electrodes overlie the pull strip. The electrodes in the two rows are exposed successively as the pull strip is pulled upwardly from the carrier sheet to facilitate access to the tabs of the electrodes.

Accordingly, it is an object of the present invention to provide an assembly for dispensing medical electrodes used in conjunction with electrocardiograph apparatus which facilitates access to the medical electrodes such that they may be easily removed and placed on a patient; and to provide an assembly for dispensing medical electrodes which is versatile and facilitates access to the electrodes without substantially increasing the cost of such an assembly.

BRIEF DESCRIPTION OF THE DRAWINGS

FIG. 4 is an exploded view of another assembly for dispensing medical electrodes in accordance with the invention; and FIG. 5 is a perspective view of the assembly illustrated in FIG. 4.

DETAILED DESCRIPTION OF THE PREFERRED EMBODIMENT

Figure 1:
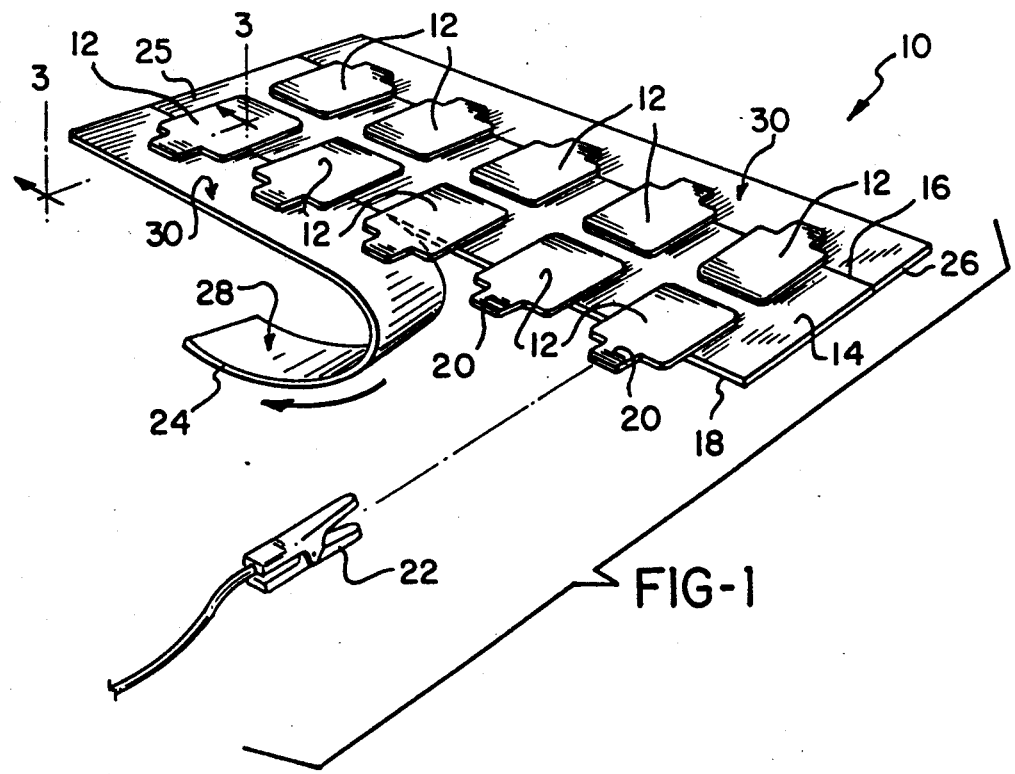
FIG. 1 is perspective view of an assembly for dispensing medical electrodes in accordance with one aspect of the invention.

FIG. 1 is a perspective view of an assembly 10 for dispensing medical electrodes generally designated by reference numeral 12 which is used in conjunction with electrocardiograph apparatus. Such electrocardiograph apparatus typically includes a lead wire clip 22. The assembly 10 comprises a carrier sheet 14 having two longitudinal tear lines 16 and 18, each spaced from the center of the carrier sheet 14. The assembly 10 includes a plurality of electrodes 12 each having a projecting tab 20. The electrodes 12 are mounted on the carrier sheet 14 such that each electrode 12 overlies one of the tear lines 16 or 18. The carrier sheet 14 may be torn along each tear line 16 and 18 so as to facilitate access to the electrodes 12. Access to the electrodes 12 is facilitated in that the undersurfaces of the tabs 20 are exposed. The tearing is accomplished by pulling the edges 24 and 26 of the carrier sheet 14. The edges 24 and 26 are created by virtue of having the tear lines 16 and 18 positioned away from the center of the carrier sheet 14. In use, the user removes the assembly 10 from any prepackaging or the like, which is not shown as it does not form part of the present invention, and tears the edge 24 substantially downwardly and away from the electrodes 12, thereby exposing the undersurfaces of the tabs 20 of the electrodes 12. Such exposure of the tabs 20 facilitates access to the electrodes 12 for the user's hand or the lead wire clip 22.

The electrodes 12 are preferably arranged on the carrier sheet 14 in two rows, which are substantially parallel to one another, such that the electrodes 12 are oriented with their respective tabs 20 extending away from the center of the carrier sheet 14. It should be appreciated by those skilled in the art that the electrodes 12 may be mounted in a variety of configurations in addition to that which is shown in FIG. 1. For example, the assembly 10 may have the electrodes 12 mounted in a single row under which a single longitudinal tear line is positioned. Alternatively, the electrodes 12 may be arranged, without departing from the scope of the invention, in two rows such that their respective tabs face inwardly toward the center of the carrier sheet 14. In this configuration, the edges 24 and 26 of the carrier sheet 14 are torn so as to expose the undersurface of the electrodes 12 themselves, as opposed to the undersurfaces of the tabs 20. Since this arrangement does not facilitate access to the tabs 20, it is not the preferred arrangement.

As stated above, the tear lines 16 and 18 are defined herein to comprise perforated lines, lines of weakening, cut lines, scored lines and other similarly classified lines of demarcation. The carrier sheet 14 will be formed from any materials known for such purposes and which will permit the formation of tear lines. The tear lines 16 and 18 each may comprise a score line being formed by scoring the bottom surface 28 of the carrier sheet 14 which is opposite the upper surface 30 upon which the electrodes 12 are mounted. The carrier sheet 14 may be scored through the entire thickness of the carrier sheet 14. Preferably, the carrier sheet 14 is scored only partially through its thickness. In this way, contaminants are prevented from seeping through either the upper surface 30 or the bottom surface 28 to any of the electrodes 12.

Figure 2:
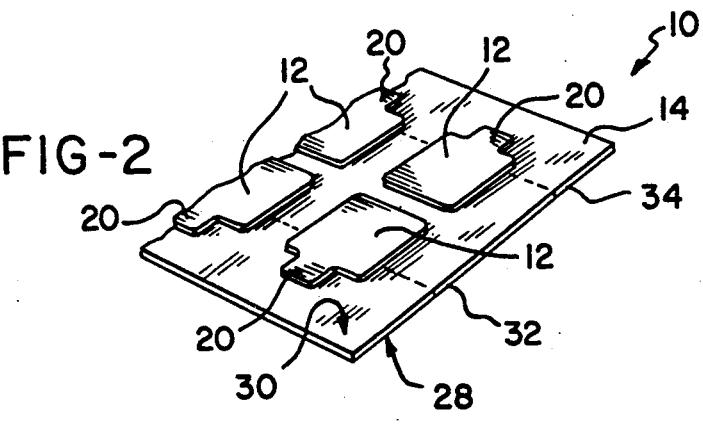
FIG. 2 is a partial perspective view of an assembly for dispensing medical having a tear line formed by perforating the carrier sheet.

Alternatively, FIG. 2 illustrates a partial perspective view of the assembly 10 having tear lines 32 and 34, each comprising perforated lines which are formed by perforating the bottom surface 28 of the carrier sheet 14. As with the scored lines described above, the perforations are preferably formed from the bottom surface 28 only partially through the thickness of the carrier sheet 14, so as to prevent any contaminants from seeping through to the electrodes 12 from either the upper surface 30 or the bottom surface 28 of the carrier sheet 14. Those skilled in the art will appreciate that other forms of tear lines beyond those described herein may be employed in the assembly 10 without departing from the scope of the invention.

Figure 3:
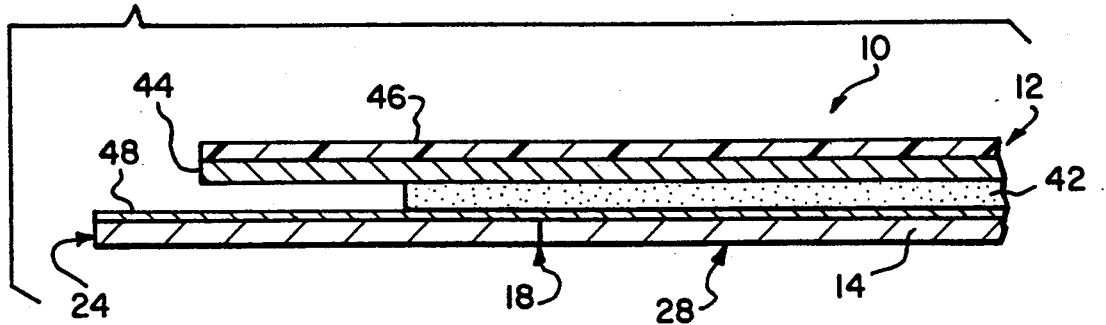
FIG. 3 is a cross-sectional view of the assembly illustrated in FIG. 1 taken along the line 3—3.

FIG. 3 is a cross-sectional view of the assembly 10 illustrated in FIG. 1 taken along line 3—3. The electrodes 12 are shown in cross section to illustrate one of the many possible medical electrodes which may dispensed by using the assembly 10 of the present invention. By way of example, the electrodes 12 comprise a conductive gel layer 42, a metal layer 44 formed on the conductive gel layer 42, and a backing layer 46 mounted on the metal layer 42. The conductive gel layer 42 may comprise any known electrolytic gel material including but not limited to Conductive Adhesive Membrane ™ (product #LT-4000), commercially available from Lec-Tec Corp. The metal layer 44 may be formed of any metal which is compatible with the conductive gel layer 42. For example, the metal layer 44 may comprise a tin foil layer. Those skilled in the art will appreciate the extensive list of materials which may be used to form the backing layer 46. Such a list includes materials such as polyethylene terephthalate (commercially available from E. I. DuPont de Nemours & Co. under the trademark Mylar ®), polystyrene, polyethylene, polypropylene and polyvinylchloride.

It should be understood that the electrodes 12 are described herein by way of example only and medical electrodes having different constructions may be used in the assembly 10. For example, medical electrodes having additional or fewer layers formed from different materials may be used without departing from the scope of the invention. In addition to the aforementioned medical electrodes, the assembly 10 may include electrodes, also referred to as electrolyte pads, which do not include a metal layer. For example, an electrolyte pad comprising an electrolyte layer and a backing layer similar to the backing layer 46 can be used in conjunction with a lead wire clip to obtain an electrocardiograph trace. The electrolyte layer will typically comprise those materials described with reference to the conductive gel layer 42. The minute voltages generated by the heart of the patient are conducted through the electrolyte pad and the lead wire clip to the electrocardiograph.

As seen in FIG. 3, the edge 24 is positioned ready for the user to tear substantially downwardly and away from the remaining portions of the carrier sheet 14. It is possible for the tear line 18 or any other tear line to extend short of the trailing end 25 of the carrier sheet 14, thereby leaving the edge 24 dangling but attached to the carrier sheet 14 after the electrodes 12 have been exposed and removed from the carrier sheet 14. Such a construction of the assembly 10 eliminates the inevitable three strips of carrier sheet 14 remaining after the electrodes 12 have been mounted on the patient. By having the tear lines 16 and 18 extending short of the trailing end 25, the edges 24 and 26 are thereby a permanent portion of the carrier sheet 14. Thus, the carrier sheet 14 may be disposed as a single piece after the electrodes 12 have been removed.

As discussed above, the carrier sheet 14 includes the tear line 18, preferably being formed from the bottom surface 28 only partially through its thickness, so as to prevent any contaminants from seeping through to the electrode 12. Such contaminants may separate the electrodes 12 from the carrier sheet 14 and alter the performance of the electrodes 12 once they are affixed to the patient. The carrier sheet 14 may be provided with a release coating 48 to allow for easy separation of the electrodes 12 from the carrier sheet 14 as the carrier sheet 14 is torn along the tear line 18. The release coating may formed from any known material which facilitates such separation. For example, the release coating 48 may comprise a silicone polymer.

Referring now to FIGS. 4 and 5, an assembly 50 for dispensing medical electrodes used in conjunction with electrocardiograph apparatus is shown. The assembly 50 generally comprises a carrier sheet 52 having a pull strip 54 releasably mounted along the longitudinal center of the carrier sheet 52. The assembly further comprises the electrodes 12 as shown in FIGS. 1-3, each having the projecting tab 20. The electrodes 12 are mounted on the carrier sheet 52 such that the tabs 20 at least partially overlie the pull strip 54, whereby the pull strip 54 may be pulled upwardly to expose the electrodes 12 for access to their respective tabs 20. The pull strip 54 is separate from the carrier sheet 52 and may be formed of the same or a different material as the carrier sheet 52. It should be understood, however, that the pull strip 54 may be, at least partially, permanently affixed to the carrier sheet 52. For example, the trailing end 56 of the pull strip 54 may be permanently secured to the trailing edge 56 of the carrier strip 52 with an adhesive material. Such a feature permits the user to dispose of a single item after the electrodes 12 have been mounted on the patient as opposed to having to dispose of the carrier sheet 52 and the pull strip 54 individually.

The pull strip 54 may have a releasable adhesive coating on its surface contacting the carrier sheet 52. It should be appreciated, however, that such an adhesive coating is not necessary since the pull strip 54 is held in position by virtue of having the electrodes 12 overlying the pull strip 54. As with the assembly 10, the electrodes 12 may be arranged in two rows which are substantially parallel. As can be clearly seen in FIG. 5, the electrodes 12 are oriented over at least one edge of the pull strip 54, such that the electrodes 12 are exposed successively as the pull strip 54 is pulled upwardly from the carrier sheet 52. The assembly 50 may have one end of the pull strip 54 curled upwardly so as to facilitate pulling the pull strip 54 away from the carrier sheet 52.

A release coating may be deposited over the carrier sheet 52 and/or the pull strip 54 to facilitate removal of the electrodes 12. In particular, a release coating over the carrier sheet 52 allows for easy separation of the pull strip 54 and the electrodes 12 from the carrier sheet 52. A release coating over the pull strip 54 facilitates separation of the pull strip 54 from the electrodes 12 as the pull strip 54 is pulled outwardly and away from the carrier sheet 52. It should be understood, however, that the configuration of the assembly 50 as well as the assembly 10 may vary in terms of size and shape without departing from the scope of the invention. For example, the pull strip 54 may have variety of shapes, lengths and widths which are compatible with the assembly 50 in that they perform the intended function of exposing the tabs 20 of the electrodes 12 such that they may be easily removed from the carrier sheet 52.

Having described the invention in detail by way of reference to preferred embodiments thereby, it will be apparent that other modifications and variations are possible without departing from the scope of the appended claims. For example, the electrodes 12 may vary in number and arrangement on the carrier sheet 14 or the carrier sheet 52.

What is claimed is:

1. An assembly for dispensing electrodes used in conjunction with electrocardiograph apparatus comprising:
   a carrier sheet;
   a pull strip releasably mounted along a longitudinal center of said carrier sheet; and
   an electrode having a projecting tab, said electrode being mounted on said carrier sheet such that said tab at least partially overlies said pull strip, whereby said pull strip may be pulled upwardly to expose said tab of said electrode for access thereto.

2. The assembly as recited in claim 1 wherein a plurality of said electrodes are arranged in first and second rows which are substantially parallel, said tab of each of said electrodes being oriented over at least one edge of said pull strip such that said electrodes in said first and second rows are exposed successively as said pull strip is pulled upwardly from said carrier sheet.

3. The assembly as recited in claim 1 wherein one end of said pull strip is curled upwardly so as to facilitate pulling said pull strip from said carrier sheet.

4. The assembly as recited in claim 1 wherein a surface of said pull strip contacting said carrier sheet includes an adhesive coating.

5. The assembly as recited in claim 1 wherein said carrier sheet includes a release coating to allow for easy removal of said pull strip and said electrode.

6. The assembly as recited in claim 1 wherein said pull strip includes a release coating to facilitate removal from said electrode as said pull strip is pulled outwardly from said carrier sheet.

7. The assembly as recited in claim 1 wherein said pull strip is permanently affixed to said carrier sheet at a longitudinal end thereof.

8. The assembly as recited in claim 1 wherein said electrode comprises an electrolyte layer and a backing member coextensively superposed onto said electrolyte layer.

9. An assembly for dispensing electrodes used in conjunction with electrocardiograph apparatus comprising:
   a carrier sheet;
   a pull strip releasably mounted along a longitudinal center of said carrier sheet; and
   a plurality of electrodes each having a projecting tab, said electrodes being mounted on said carrier sheet in first and second rows such that said tabs of said electrodes overlie said pull strip, whereby said electrodes in said first and second rows are exposed successively as said pull strip is pulled upwardly from said carrier sheet to facilitate access to said tabs of said electrodes.

* * * * *